(12) United States Patent
Thate

(10) Patent No.: US 10,702,129 B2
(45) Date of Patent: Jul. 7, 2020

(54) METHOD FOR PROCESSING AN ENDOSCOPE

(71) Applicant: OLYMPUS WINTER & IBE GMBH, Hamburg (DE)

(72) Inventor: Henning Thate, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 201 days.

(21) Appl. No.: 15/782,970

(22) Filed: Oct. 13, 2017

(65) Prior Publication Data

US 2018/0103830 A1 Apr. 19, 2018

(30) Foreign Application Priority Data

Oct. 14, 2016 (DE) .......................... 10 2016 220 137

(51) Int. Cl.
| | |
|---|---|
| *A61B 1/00* | (2006.01) |
| *A61L 2/24* | (2006.01) |
| *A61B 1/12* | (2006.01) |
| *G01M 3/28* | (2006.01) |

(52) U.S. Cl.
CPC .......... *A61B 1/00057* (2013.01); *A61B 1/123* (2013.01); *A61B 1/125* (2013.01); *A61L 2/24* (2013.01); *G01M 3/2846* (2013.01)

(58) Field of Classification Search
CPC ..... A61B 1/00057; A61B 1/123; A61B 1/125; A61L 2/24; G01M 3/2846
See application file for complete search history.

(56) References Cited

U.S. PATENT DOCUMENTS

| | | | | |
|---|---|---|---|---|
| 5,795,403 | A * | 8/1998 | Biermaier | ............. B08B 9/0325 134/166 C |
| 6,412,334 | B1 * | 7/2002 | Kral | ................... A61B 1/00057 73/40 |
| 2005/0056081 | A1 * | 3/2005 | Gocho | ................. G01M 3/2815 73/40 |
| 2007/0238923 | A1 * | 10/2007 | Kubach | ................... G01M 3/26 600/118 |
| 2009/0220377 | A1 * | 9/2009 | Hasegawa | ............... A61B 1/123 422/28 |
| 2016/0202139 | A1 * | 7/2016 | Philipp | ................ G01M 3/2815 73/49.5 |

FOREIGN PATENT DOCUMENTS

DE 102012218754 A1 4/2014

* cited by examiner

*Primary Examiner* — Randy W Gibson
*Assistant Examiner* — Gedeon M Kidanu
(74) *Attorney, Agent, or Firm* — Scully, Scott, Murphy & Presser, P.C.

(57) ABSTRACT

A method for reprocessing an endoscope for the implementation of leak testing the endoscope, the method including: connecting the endoscope in an airtight manner to a compressed air hose, which is operatively connected to a compressed air source; subjecting the endoscope to compressed air up to a predetermined pressure level via the compressed air hose; during the pneumatic leak measurement and after opening of an outlet valve, measuring a temporal course of air pressure in the endoscope without any further compressed air supply; measuring a temporal change of the air pressure at the outlet valve; and determining one of a tightness of the endoscope or a leakage of the endoscope based on a temporal gradient of the temporal change of the air pressure.

6 Claims, 1 Drawing Sheet

METHOD FOR PROCESSING AN ENDOSCOPE

CROSS-REFERENCE TO RELATED APPLICATION

The present application claims the benefit to DE 10 2016 220 137.9 filed on Oct. 14, 2016, the entire contents of which is incorporated herein by reference.

BACKGROUND

Field

The present application relates to a method for reprocessing an endoscope, such as a flexible endoscope, wherein for the implementation of leak testing an endoscope to be processed is connected in an airtight manner to a compressed air hose.

Prior Art

For the reprocessing of endoscopes, such as flexible endoscope, cleaning and disinfecting apparatuses (referred to as "RDG-Es") are commonly used which are based on a chemical-thermal reprocessing process. In order to avoid damage to the endoscope by the cleaning liquid, it is important that the outer sheath of the endoscope is completely intact and thus the cleaning liquid cannot penetrate into the interior of the endoscope. Before the first introduction of water in the "RDG-E", this is tested by pumping the endoscope to an overpressure via a suitable interface. Then pressure is monitored for a decrease in pressure, wherein due to such pressure drop a leak in the endoscope can be indicated. In case of a failed test or at the end of the process, namely at the end of the cleaning and disinfecting process, the endoscope is again partially aired. The reprocessing process itself is carried out at a slight overpressure in the endoscope.

Suitable "RDG-E" systems are available from OLYMPUS Winter & Ibe GmbH, Hamburg, under the name "ETD". These systems include a so-called "Leak Tester", which is used for leak testing. In such a test, after the start of the program, an endoscope is initially pumped to an overpressure of, e.g., 285 mbar, and then, following the leak test, the overpressure is reduced to ca. 150 mbar above the ambient pressure. This pressure is maintained during the reprocessing process, and is continuously monitored, so as to preclude penetration of water from the exterior.

When an endoscope is used in endoscopy, occasionally damage occurs, such as the endoscope may be punctured from biopsy channels. A micro-perforation may be created which might not be detected in a leak test under certain circumstances. When a subsequent reprocessing process is carried out, rinsing water and clear water are passed through the channels which are to be rinsed, at a pressure which is appreciably greater than 150 mbar. As a result, water can be transferred from the channel rinsing into the region of the endoscope to be protected, which leads to increased pressure in the endoscope, above 150 mbar. The Leak Tester reacts to this by releasing compressed air from the endoscope, in order to maintain the overpressure at 150 mbar. In this way, water can penetrate into the tubing through the air outlet pathway, and ultimately into the Leak Tester, resulting in damage to or even ruining of the Leak Tester.

In performing leak testing on surgical instruments, such as endoscopes, the endoscope is connected to a leak testing device to determine whether the outer sheath of the endoscope and the channels of the endoscope are completely intact.

Before the first cleaning operation with a liquid, e.g. water, a test is conducted by connecting the leak testing device to the endoscope via a suitable connection, and then pumping to an overpressure. Then monitoring for decreasing of the pressure is carried out, in order to determine whether there is a leak in the endoscope.

In the event of a leaking endoscope, if water is present then water which has penetrated can in turn penetrate into the RDG-E when air is exhausted, which will damage the RDG-E.

In order to detect the leak, the endoscope is brought to a test pressure, typically 275 to 300 mbar, before the endoscope cleaning operation is carried out, and then a leak test is conducted for a specific time, e.g. 60 seconds. If the pressure inside the endoscope decreases by more than a previously established amount, typically between 10 to 15 mbar, the endoscope is considered to be leaking, and consequently the subsequent reprocessing is not performed.

If present leak testing methods are employed, inaccuracies arise, in that certain types of leaks, especially directionally dependent leaks, cannot be detected reliably.

SUMMARY

Starting from this prior art, it is an object to improve the leak testing in a simple manner, such as during carrying out an automated leak test in a reprocessing device.

Such object can be achieved by a method for reprocessing an endoscope, such as a flexible endoscope, wherein, for the implementation of leak testing the endoscope to be processed is connected in an airtight manner to a compressed air hose, which is connectable or connected to a compressed air source, wherein for the implementation a pneumatic leak test, the endoscope is subjected to compressed air up to a predetermined or predeterminable pressure level via the compressed air hose, wherein during the pneumatic leak measurement. after opening of an outlet valve a temporal course of the air pressure in the endoscope is measured without any further compressed air supply, wherein the temporal change of the air pressure at the outlet valve is determined and the tightness of the endoscope or the leakage of the endoscope is determined in dependency of the temporal gradient of the temporal change of the air pressure.

In the case of an endoscope, the outlet valve of the endoscope can be briefly opened on the input side before carrying out the reprocessing operations in order to detect leaks based on the rate at which the pressure on the outlet side rises (again).

According to the prior art, in the conventional methods of leak detection, e.g. for leak testing of an endoscope, the temporal course of the pressure equalization is determined in each case. However, with an endoscope having a high packing density, the (pressure) equalization processes in the endoscope may require a relatively long time period, of one minute or longer. The time duration of these equalization processes corresponds to approximately the duration of the customary leak test according to the prior art. Here, testing is conducted as to whether the pressure measured in the connection to the endoscope decreases over the entire period of, e.g., one minute, even with an intact endoscope, where the endoscope has a high packing density, so that the technical measurement method cannot distinguish between a leak and the pressure equalization in endoscopes having a high packing density.

In contrast, the temporal change of the air pressure can be determined over a short period, less than 20 seconds, thus providing a simple and reliable method of leak testing which is applicable even to endoscopes having a high packing density, depending on the temporal gradient. Thus, with the aid of the temporal gradient of the temporal change of the air pressure, leaks can be detected even in endoscopes having a high packing density. In this connection, following a brief opening of the outlet valve, the rate at which the pressure rises on the outlet side due to internal pressure equalization processes in the endoscope which cause a reversal of the effect can be determined. Here, the rate at which the pressure rises on the outlet side corresponds to the temporal gradient of the temporal change of the air pressure. As a result of the high packing density in endoscopes, pressure equalization processes take place such that, when an exhausting occurs then immediately after the opening of the outlet valve the pressure undergoes a reversal of effect, with an increase of the pressure. Following the pressure decrease, a continuous pressure increase takes place within the volume of the leak detector itself, up to a maximum value.

In the case of an endoscope with a leak, the initial rate of increase of the pressure on the outlet side will be less than the rate of temporal change and thus the temporal gradient of the air pressure in the case of an airtight endoscope.

Therefore, given a constant inherent volume or dead volume of the leak testing device, the pressure increase after the opening of the outlet valve will occur over a predetermined, relative short time period.

According to an embodiment of the method, it is provided that, in the event that a predetermined gradient set-point value for the temporal change of the air pressure is exceeded, the tightness of the endoscope can be determined. In an intact, i.e. airtight, endoscope, the temporal gradient of the change of the air pressure is greater than the initial temporal gradient of the pressure change in a non-tight endoscope.

In this connection, the respective specific set-points of the gradients are determined in advance of carrying out the method for various endoscopes, and, e.g., said set-points are entered into a databank or an electronic memory. In carrying out the reprocessing with the aid of the stored specific set-points of the gradients, the given gradient set-point for a specific endoscope or type of endoscope can be used for determining the airtightness of the endoscope which is to be processed.

According to another embodiment of the method, it is provided that, in the event that the gradient of the temporal change of the air pressure falls below a predetermined gradient set-point value, the leakage of the endoscope can be determined.

Furthermore, another embodiment of the method is distinguished in that it provides that the temporal increase of the pressure after the opening of the outlet valve can be determined and/or the temporal change thereof can be determined, such as exclusively.

The outlet valve can be opened for a duration of less than 20 seconds, such as less than 10 seconds or less than 5 seconds.

BRIEF DESCRIPTION OF THE DRAWINGS

Additional features will be apparent from the following description of certain embodiment, together with the claims, and the accompanying drawings. Embodiments may be comprised of individual features or a combination of a plurality of features.

Without limiting the scope of the general inventive concept, the embodiments will be described below with the aid of exemplary embodiments, with reference to the drawings; in this connection, reference is made explicitly to the drawings regarding all features not described in detail in the text.

In the drawings:

FIG. 1 illustrates a schematic representation of a cleaning and disinfection apparatus; and FIG. 2 illustrates schematically a pressure profile across a length of a shaft of an airtight endoscope and a leaking endoscope.

DETAILED DESCRIPTION

Figure 1:
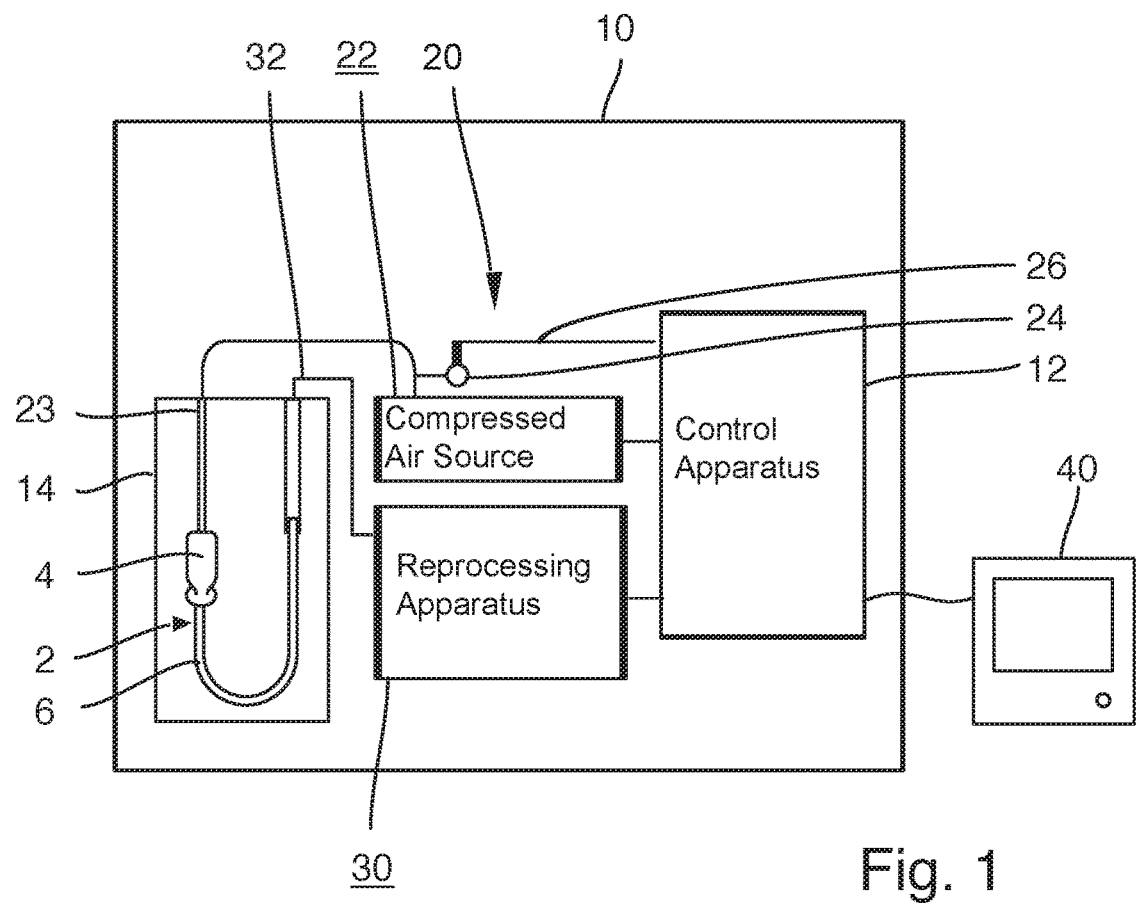

In the drawings, identical or similar elements and/or parts have been assigned the same reference numerals, to avoid providing a new representation in each instance.

FIG. 1 shows schematically a reprocessing system 10, with a flexible endoscope 2 being disposed in the cleaning chamber 14 of said system 10; the endoscope is about to be cleaned and disinfected. The endoscope 2 comprises a grip 4 and a flexible shaft 6, both of which are connected to connections of the reprocessing system 10.

The shaft 6 of the endoscope is connected via connecting means to a reprocessing apparatus 30 of the processing system 10, which is provided for reprocessing the endoscope, and the hand grip 4 is connected via a compressed air hose 23 with a compressed air source 22, e.g. a compressor, to the apparatus 20 for applying compressed air (referred to as "leakage tester"). This, along with the reprocessing apparatus 30, is connected to a control apparatus 12 of the reprocessing system 10, which is thus a control apparatus for the reprocessing apparatus 30 and the apparatus 20 for applying compressed air. The reprocessing apparatus 30 and the control apparatus 12 can be one or more controllers, such as one or more CPUs.

At the output of the compressed air source 22 an air pressure sensor 24 is connected to the compressed air hose 23, which sensor measures the overpressure in the compressed air hose 23 compared to the ambient pressure and sends corresponding signals via signal line 26 also to the control apparatus 12 of the reprocessing system 10. The control apparatus 12 is also connected to a display apparatus 40 by means of which the control apparatus 12 can be influenced from the exterior, and by means of which data from the control apparatus 12, e.g. overpressure measurement data from the air pressure sensor 24 and/or process data, can be displayed.

The apparatus 20 for applying compressed air is connected via a compressed air hose 23 to the endoscope 2 (shown only schematically), whereby compressed air is pumped into the endoscope 2 and is later withdrawn.

An air pressure sensor 24 is connected to the compressed air hose 23, which sensor measures the pressure of the compressed air in the compressed air hose 23 and in the endoscope 2. Alternatively, the air pressure sensor 24 may directly measure the air pressure at the endoscope 2 or at the outlet of the compressed air source 22.

Figure 2:
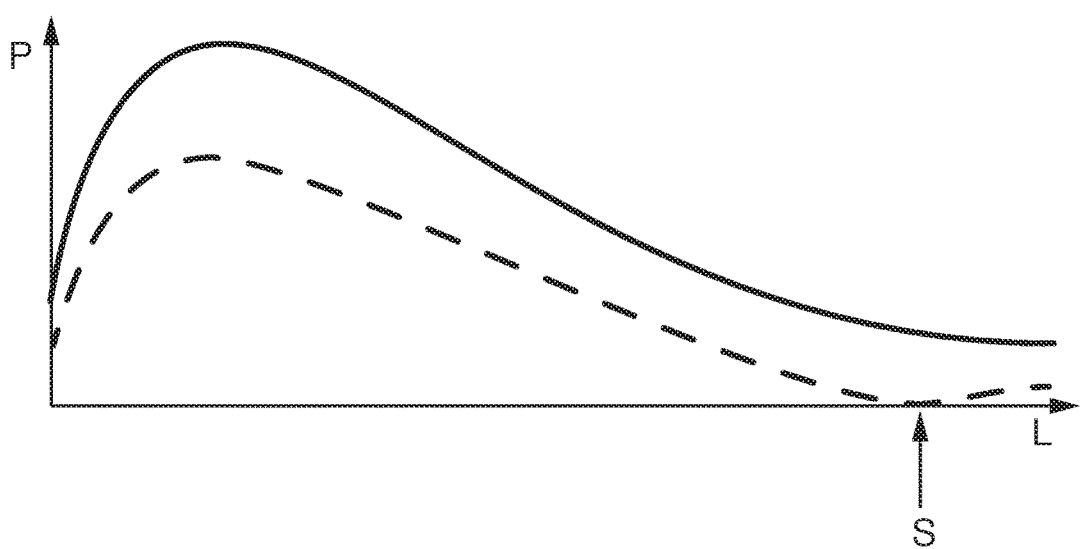

In FIG. 2, the solid line represents the pressure versus length in the interior of an airtight endoscope, and the dashed line represents pressure versus length in the interior of a leaking endoscope immediately after a brief opening of an outlet valve. When leak testing an endoscope, the rate at which the pressure reestablishes itself on the outlet side after brief opening of the outlet valve, and thus the temporal gradient of the temporal change in pressure during discharge, is taken into account, and is determined, respectively, in light of the fact that in the case of an airtight endoscope the pressure at the outlet valve rises again, in consequence of pressure equalization processes.

In the leaking endoscope (see dashed line), the rate, i.e. the temporal gradient of the temporal change of the air pressure is less, since the pressure at the inlet valve, or respectively the pressure increase, is lower, because of the leakage and because of the pressure equalization compensating processes, since at the same time a compensating process also takes place towards the leak location (indicated by S).

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Endoscope
4 Hand grip
6 Flexible shaft
10 Reprocessing system
12 Control apparatus
14 Cleaning chamber
20 Apparatus for applying compressed air
22 Source of compressed air
23 Compressed air hose
24 Air pressure sensor
26 Signal line
30 Reprocessing apparatus
32 Rinsing hose
40 Display unit
S Location of leak

The invention claimed is:

1. A method for reprocessing an endoscope for implementation of leak testing the endoscope, the method comprising:
   connecting the endoscope in an airtight manner to a compressed air hose, which is operatively connected to a compressed air source;
   supplying the endoscope with compressed air from the compressed air source up to a predetermined pressure level via the compressed air hose;
   opening an outlet valve to release compressed air from the endoscope;
   during a time period in which the outlet valve is open, stopping the supply of compressed air from the compressed air source;
   during the time period in which the outlet valve is opened and the supply of compressed air is stopped, measuring a temporal course of air pressure in the endoscope;
   measuring a temporal change of the air pressure at the outlet valve; and
   determining one of a tightness of the endoscope or a leakage of the endoscope based on a temporal gradient of the temporal change of the air pressure;
   wherein, where a gradient set-point value for the temporal gradient of the temporal change of the air pressure is exceeded, the tightness of the endoscope is determined.

2. The method according to claim 1, wherein one or more of the temporal change of the air pressure after the opening of the outlet valve is determined or the temporal change thereof is determined.

3. The method according to claim 1, wherein the time period during which the outlet valve is opened is less than 20 seconds.

4. The method of claim 3, wherein the time period during which the outlet valve is opened is less than 10 seconds.

5. The method of claim 3, wherein the time period during which the outlet valve is opened is-less than 5 seconds.

6. A method for reprocessing an endoscope for the implementation of leak testing the endoscope, method comprising:
   connecting the endoscope in an airtight manner to a compressed air hose, which is operatively connected to a compressed air source;
   supplying the endoscope with compressed air from the compressed air source up to a predetermined pressure level via the compressed air hose;
   opening an outlet valve to release compressed air from the endoscope;
   during a time period in which the outlet valve is open, stopping the supply of compressed air from the compressed air source;
   during the time period in which the outlet valve is opened and the supply of compressed air is stopped, measuring a temporal course of air pressure in the endoscope;
   measuring a temporal change of the air pressure at the outlet valve; and
   determining one of a tightness of the endoscope or a leakage of the endoscope based on a temporal gradient of the temporal change of the air pressure;
   wherein, in the event that the temporal gradient of the temporal change of the air pressure falls below a gradient set-point value, the leakage of the endoscope is determined.

* * * * *